US012746346B2

(12) United States Patent
Kassab

(10) Patent No.: US 12,746,346 B2
(45) Date of Patent: Sep. 29, 2026

(54) INTRANODAL NEEDLE AND METHOD OF USING THE SAME

(71) Applicant: Ghassan S. Kassab, La Jolla, CA (US)

(72) Inventor: Ghassan S. Kassab, La Jolla, CA (US)

( * ) Notice: Subject to any disclaimer, the term of this patent is extended or adjusted under 35 U.S.C. 154(b) by 386 days.

(21) Appl. No.: 18/685,089

(22) PCT Filed: Aug. 19, 2022

(86) PCT No.: PCT/US2022/040930
§ 371 (c)(1),
(2) Date: Feb. 20, 2024

(87) PCT Pub. No.: WO2023/023353
PCT Pub. Date: Feb. 23, 2023

(65) Prior Publication Data
US 2024/0350747 A1 Oct. 24, 2024

Related U.S. Application Data

(60) Provisional application No. 63/234,901, filed on Aug. 19, 2021.

(51) Int. Cl.

| | |
|---|---|
| ***A61M 5/42*** | (2006.01) |
| ***A61M 5/00*** | (2006.01) |
| *A61B 8/00* | (2006.01) |

(52) U.S. Cl.
CPC ............ *A61M 5/427* (2013.01); *A61M 5/007* (2013.01); *A61B 8/483* (2013.01);
(Continued)

(58) Field of Classification Search
CPC ........ A61B 17/3403; A61B 2090/3983; A61B 34/20; A61B 2034/2046; A61B 2034/2065; A61B 2017/3413; A61B 2090/3925; A61B 2034/2063; A61B 2017/00026; A61B 5/418; A61M 5/427; A61M 2230/65
See application file for complete search history.

(56) References Cited

U.S. PATENT DOCUMENTS 6,205,352 B1 * 3/2001 Carroll ............... A61K 49/0023
424/9.4
8,540,639 B2 * 9/2013 Kusminsky ............ A61B 8/481
424/9.1

(Continued)

FOREIGN PATENT DOCUMENTS

JP 2005532841 A * 11/2005 ............. A61B 5/412
WO WO-2017154503 A1 * 9/2017 ............ A61M 5/168
WO WO-2020210710 A1 * 10/2020 ............... A61B 8/12

OTHER PUBLICATIONS

International Searching Authority, International Search Report, PCT/US22/40930, Dated Jan. 11, 2023.

(Continued)

*Primary Examiner* — William R Carpenter
(74) *Attorney, Agent, or Firm* — Abd Almonem Doolaanea

(57) ABSTRACT

Intranodal needle and method of using the same. The present disclosure includes disclosure of a method, comprising inserting a tip of a needle through the skin and into a tissue selected from the group consisting of a lymph node and a thoracic duct, and delivering an immune modulating agent through the needle and into the tissue to treat at least one immune disorder.

17 Claims, 3 Drawing Sheets

(52) U.S. Cl.
CPC . *A61M 2205/3334* (2013.01); *A61M 2210/10* (2013.01); *A61M 2230/65* (2013.01)

(56) References Cited

U.S. PATENT DOCUMENTS

| | | | | |
|---|---|---|---|---|
| 2003/0105410 | A1* | 6/2003 | Pearlman | A61B 90/17 600/547 |
| 2009/0093807 | A1* | 4/2009 | Hyde | A61B 5/0084 606/34 |
| 2009/0210029 | A1* | 8/2009 | Tsui | A61B 5/6848 607/46 |
| 2013/0310822 | A1* | 11/2013 | Mayse | A61B 18/1815 606/27 |
| 2015/0359991 | A1* | 12/2015 | Dunbar | A61B 8/4254 600/424 |
| 2017/0007186 | A1* | 1/2017 | Baek | A61B 5/021 |

OTHER PUBLICATIONS

International Searching Authority, Invitation to Pay Additional Fees and, Where Applicable, Protest Fee, PCT/US22/40930, Dated Nov. 1, 2022.

* cited by examiner

INTRANODAL NEEDLE AND METHOD OF USING THE SAME

PRIORITY

The present patent application is related to, claims the priority benefit of, and is a U.S. 35 U.S.C. 371 national stage patent application of, International Patent Application Serial No. PCT/US22/40930, filed Aug. 19, 2022, which is related to, and claims the priority benefit of, U.S. Provisional Patent Application Ser. No. 63/234,901, filed Aug. 19, 2021, the contents of which are incorporated herein directly and by reference in their entirety.

BACKGROUND

Intra-lymph node injection recently became a new pathway for delivering immune modulating agents (vectors) for cancer treatment (CAR T cells) and immune disorder therapies. The main rationale is the ability to expose the majority of delivered vector to the specific population of the T cells that resides in the lymphatic system.

One major concern of this therapy is the overall cost, whereby one CAR T cell "cocktail" can cost approximately US$300,000. As such, it is important to ensure that the therapy is properly introduced and delivered without losing any such therapeutic due to leakage.

In view of the same, methods of delivering intra-lymph therapeutics with high precision and minimal to no leakage would be well received in the medical arts.

BRIEF SUMMARY

The present disclosure includes disclosure of a method, comprising inserting a tip of a needle through the skin and into a tissue selected from the group consisting of a lymph node and a thoracic duct, and delivering an immune modulating agent through the needle and into the tissue to treat at least one immune disorder.

The present disclosure includes disclosure of a method, wherein the step of inserting further comprises confirming a location of the tip of the needle within the tissue.

The present disclosure includes disclosure of a method, wherein the step of inserting further comprises confirming efferent flow from the tissue.

The present disclosure includes disclosure of a method, wherein the step of inserting further comprises securing the needle into the tissue.

The present disclosure includes disclosure of a method, further comprising the step of monitoring the delivery of the immune modulating agent and detecting potential leakage outside of the tissue or the venous system during the delivery.

The present disclosure includes disclosure of a method, wherein the step of inserting is performed under ultrasound guidance.

The present disclosure includes disclosure of a method, wherein the ultrasound guidance comprises using a three-dimensional ultrasonic probe.

The present disclosure includes disclosure of a method, wherein the three-dimensional ultrasonic probe comprises a portion of a needle guide system comprising the needle, and wherein the three-dimensional ultrasonic probe is operable while the tip of the needle is positioned within the tissue.

The present disclosure includes disclosure of a method, wherein the step of inserting is performed to position the tip of the needle at a center of the lymph node.

The present disclosure includes disclosure of a method, wherein the step of inserting is performed to position the tip of the needle near a hilum of the lymph node.

The present disclosure includes disclosure of a method, wherein the step of inserting is performed using photoacoustic imaging.

The present disclosure includes disclosure of a method, wherein the photoacoustic imaging comprises the step of injecting a photoacoustic contrast agent with affinity to the lymphatic system proximal to the tissue.

The present disclosure includes disclosure of a method, further comprising the use of image processing software to calculate an ideal position for the needle tip within the tissue after the photoacoustic contrast agent has migrated into the tissue so that the photoacoustic imaging can identify the tissue having the photoacoustic contrast agent.

The present disclosure includes disclosure of a method, performed so that efferent lymphatic vessels receive the photoacoustic contrast agent and become opaque under photoacoustic imaging.

The present disclosure includes disclosure of a method, performed so that lymph nodes having lympho-venous communications do not receive the photoacoustic contrast agent and therefore do not become opaque under photoacoustic imaging.

The present disclosure includes disclosure of a method, wherein the step of inserting is performed using impedance based upon bioimpedance differences of the skin and the tissue.

The present disclosure includes disclosure of a method, wherein the bioimpedance differences are determined using an impedance device with a first electrode and a second electrode, whereby the first electrode is located at the tip of the needle and whereby the second electrode is located at a proximal portion of the needle or on a surface of the skin.

The present disclosure includes disclosure of a method, wherein the bioimpedance differences can detect leakage of the immune modulating agent during or after delivery into the tissue.

The present disclosure includes disclosure of a method, wherein the step of delivering is performed using impedance based upon bioimpedance differences of the skin, the tissue, and a vein.

The present disclosure includes disclosure of a method, wherein the bioimpedance differences are determined using the needle as one electrode, a second electrode positioned on the skin, and a third electrode positioned within a vein.

The present disclosure includes disclosure of a method, wherein the bioimpedance differences are identified if there is leakage of the immune modulating agent into the vein.

The present disclosure includes disclosure of a method, wherein the step of inserting is performed using a motorized needle device.

The present disclosure includes disclosure of a method, wherein the step of inserting comprises inserting the needle that is coated with an echogenic material configured to be visualized using an external visualization mechanism.

The present disclosure includes disclosure of a method, wherein the step of delivering is performed using hydrostatic pressure.

The present disclosure includes disclosure of a method, wherein the step of delivering is performed using pressure-regulated injection.

The present disclosure includes disclosure of a method, wherein the step of delivering is performed using flow-regulated injection.

The present disclosure includes disclosure of a method, wherein the step of delivering is performed using an immune modulating agent marked with an indicator configured to be visualized under ultrasound so that potential leakage of the immune modulating agent outside of the tissue can be visualized.

The present disclosure includes disclosure of a method, wherein the step of delivering is performed using an immune modulating agent marked with an indicator configured to be visualized under photoacoustic imaging so that potential leakage of the immune modulating agent outside of the tissue can be visualized.

The present disclosure includes disclosure of a method, wherein the step of delivering is performed while a Doppler probe is positioned adjacent an iliac vein.

The present disclosure includes disclosure of a method, wherein the immune modulating agent is marked with an indicator, and wherein the Doppler probe is configured to detect a signal from the immune modulating agent within the iliac vein should the immune modulating agent leak into the iliac vein.

The present disclosure includes disclosure of a method, wherein the step of inserting is further performed to secure the tip of the needle within the tissue using a needle securing device.

The present disclosure includes disclosure of a method, further comprising the step of identifying the tissue among a collection of tissues, the step of identifying performed before the step of inserting.

The present disclosure includes disclosure of a method, wherein the identifying step is performed by injecting a photoacoustic contrast agent with affinity to the lymphatic system proximal to the collection of tissues, and monitoring the photoacoustic contrast agent as it is received by efferent lymphatic vessels within the collection of tissues.

The present disclosure includes disclosure of a method, wherein the identifying step further comprises the step of selecting the tissue from the efferent lymphatic vessels that received the photoacoustic contrast agent.

The present disclosure includes disclosure of a method, wherein the step of delivering is performed while monitoring efferent flow of the immune modulating agent into and through the tissue using a monitoring mechanism selected from the group consisting of bioimpedance, Doppler, photoacoustic, and ultrasound.

The present disclosure includes disclosure of a method, wherein the step of delivering is performed while monitoring efferent flow of the immune modulating agent into and through the tissue.

The present disclosure includes disclosure of a method, further comprising the step of securing the needle within the tissue prior to the step of delivering the immune modulating agent.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

Figure 1:
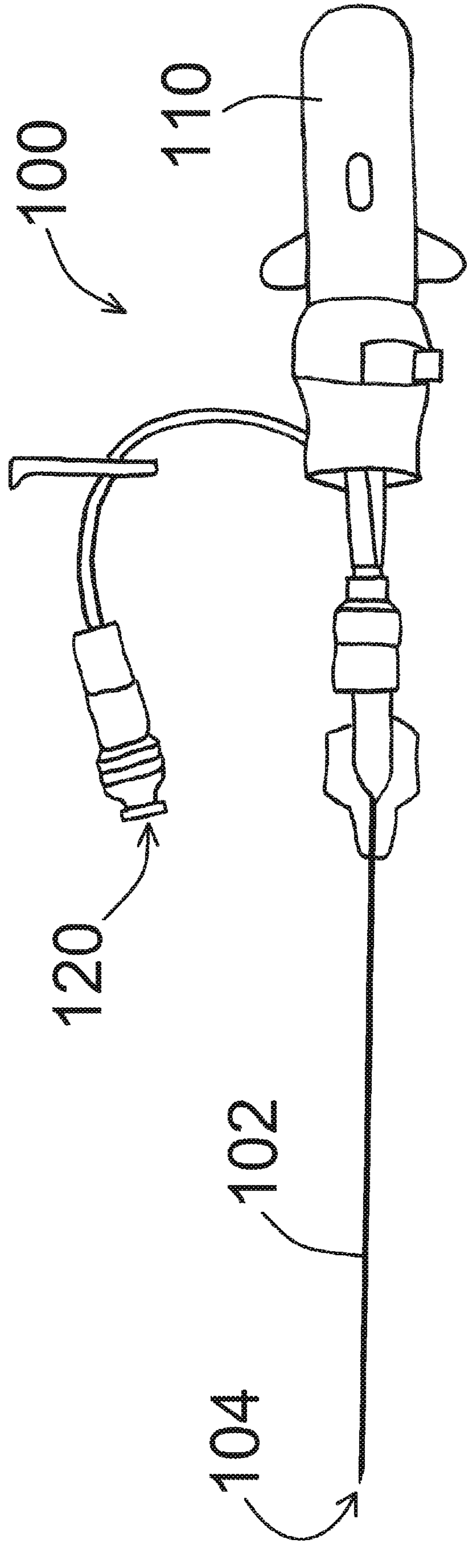
FIG. 1 shows the full needle device, according to at least one embodiment of the present disclosure.
Figure 2:
FIG. 2 shows the proximal end of an exemplary needle device showing an ergonomic handle with "wings" that activates spring loading and "button" that releases the spring to puncture the lymph node, according to at least one embodiment of the present disclosure. This is important because "jabbing" of lymph node is needed to avoid the slipping of node with slower approach.

As such, an overview of the features, functions and/or configurations of the components depicted in the various figures will now be presented. It should be appreciated that not all of the features of the components of the figures are necessarily described and some of these non-discussed features (as well as discussed features) are inherent from the figures themselves. Other non-discussed features may be inherent in component geometry and/or configuration. Furthermore, wherever feasible and convenient, like reference numerals are used in the figures and the description to refer to the same or like parts or steps. The figures are in a simplified form and not to precise scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Intra-lymph node injection recently became a new pathway for delivering immune modulating agents (vectors) for cancer treatment (CAR T cells) and immune disorder therapies. The main rationale is the ability to expose the majority of delivered vector to the specific population of the T cells that resides in the lymphatic system.

The most logical site to deliver vector is in the inguinal lymph nodes where these lymph nodes are located superficially and easily accessible. The delivery is performed through the needle positioned in the lymph node. In additional embodiments, the delivery is performed through the catheter positioned in the lymph node or directly into the thoracic duct.

It is important that the device needed is configured to deliver vector dose in its entirety into the lymph node efferent lymphatics. Such a device should effectively:

a. be used in connection with a technically simple and scalable method of placement of the needle into lymph node;

b. confirm the position of the needle in the lymph node and efferent flow from lymph node;

c. secure the needle in the tissues; and d. monitor the injection and detection of the leak outside lymph node and/or venous system while injecting of the vector into lymph node.

A. Technically Simple and Reproducible Placement of the Needle into Lymph Node

An exemplary device 100 of the present disclosure is shown in FIG. 1. The needle 102 of an exemplary device 100 of the present disclosure can be placed under ultrasound (US) guidance. The ideal location of the tip 104 of the needle 102 is the center of the lymph node, close to the hilum of the node. An exemplary device 100 of the present disclosure can also comprise a handle 110 to facilitate needle 102 delivery.

In at least one embodiment, and to assure the precise placement of the needle 102, the US will identify the borders of the lymph nodes as well as long access of the lymph node.

The borders of the lymph node will be identified automatically using image processing of US images, and the ideal location of the needle 102 will be identified and mark in three-dimensional space. The needle 102 will be then advanced into the desired location.

In some embodiments, a three-dimensional (3D) US probe will be used to identify the border of the lymph node.

In at least some embodiments, photoacoustic imaging will be used to identify the lymph node as follows: a small amount of the photoacoustic contrast agent with affinity to the lymphatic system (ISG and or patent blue) will be injected in the skin proximal to the lymph node. This type of contrast agent is absorbed exclusively by the lymphatic system. Using photoacoustic imaging, the lymph node and efferent lymphatic vessels will be identified. Using an image processing software, the ideal position of the needle 102 in the lymph node will be then calculated.

Impedance system can be used to confirm the position of the needle 102 in the lymph node based on differences in bioimpedance of skin, tissue and lymph node. The conductivity of the lymph nodes is different from the conductivity of the fat (inguinal lymph nodes are positioned in the subcutaneous fat). When the needle 102 is positioned in the lymph node, the impedance will be lower than in the soft tissue. The first electrode will be positioned at the tip 104 of the needle 102 and the second at the proximal part of the needle 102 or on the surface of the skin. Bio-impedance recordings can detect leakage of injected solution external to the lymph as this will decrease the impedance or increase conductance (inverse of impedance).

In at least one embodiment, the needle 102 can be attached to the needle guide system that will be attached to the US probe.

In various embodiments, the needle 102 will be advanced using motorized device.

In some embodiments, the lymph node needle 102 will be coated with echogenic material (micro or nano-beads) to enhance visualization of the needle 102.

In at least one embodiment, the needle 102 will be connected to an injection port under hydrostatic pressure (gravity) or pressure- or flow-regulated injections at set pressures or flow rates, respectively.

B. Confirmation of Efferent Flow from Lymph Node

A key requirement for the lymph node needle 102 is the ability to deliver the treatment dose of the vector in its entirety into efferent lymphatics ducts. To confirm the position of the needle 102, ultrasound contrast will be injected through the needle 102. Observation of the opacification of the efferent lymphatic vessels will confirm the egress of the contrast through the efferent lymphatic vessels. Lymphovenous communications often exist in the lymph node. These communications present significant challenge for intranodal injection because the injection material may be delivered into the venous system instead of efferent lymphatics. There are several ways to detect the leakage as described below.

i. Impedance technique: the needle 102 in the lymph node will serve as one electrode. The second electrode will be positioned in the soft tissues. The third electrode will be positioned in the vein. In case there is a leakage of the vector into vein, the impedance between lymph node and vein will be detected.

ii. Visualization of the leakage of the contrast into outside lymph node and/or vein. Vector will be marked with the US/photoacoustic dye/indicator, so that US/photoacoustic can detect it.

iii. Doppler method: The doppler probe will be positioned above the injection site pointing onto iliac vein. In case US contrast leaks into vein, the doppler will detect the signal from US contrast.

C. Securing the Needle in the Tissues

Figure 3:
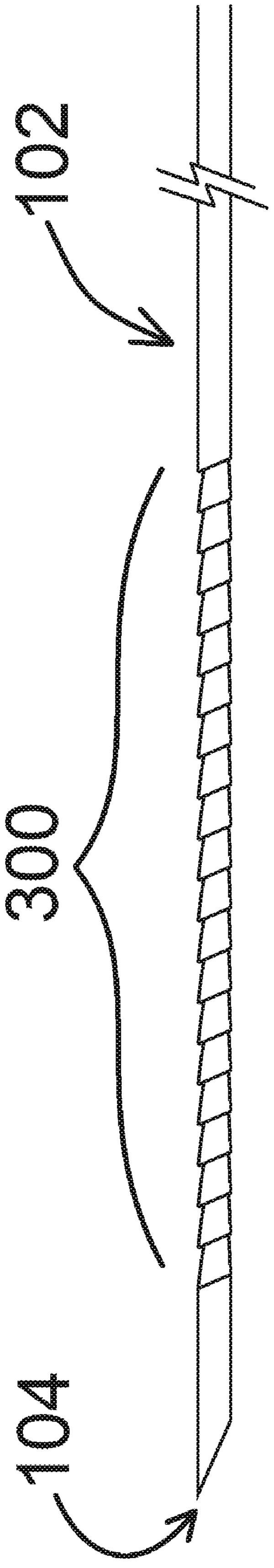
FIG. 3 shows the distal end of an exemplary needle device, with helical grooves to increase the retention force of the needle in the lymph, according to at least one embodiment of the present disclosure.

A special securing device will be attached designed and attached as disclosed previously including grooves (grooved section 300, as shown in FIG. 3) in the needle 102 (e.g., helical and other geometries) that increase the frictional forces with the tissue ensure higher retention forces.

D. Monitoring of the Injection and Detection of the Leak Outside Lymph Node and/or Venous while Injecting of the Vector into Lymph Node One of the most important tasks during injection is to make sure that the full vector dose will be delivered into efferent lymphatic vessels. Several mechanisms can be utilized to identify the leak, as follows:

i. Impedance measurement between lymph node, vein, and soft tissue. In the case there is a leakage the impedance will change accordingly since the impedance of the injected solution or cells is generally lower than that of tissue.

ii. Doppler signal positioned on the iliac vein.

iii. Continuous visualisation of the vector marked with contrast using either photoacoustic and/or US contrast techniques iv. Pressure controlled injection. When the leakage occurs, the pressure drop increases due to increased flow.

In view of the foregoing:

The present disclosure includes disclosure of a method, comprising inserting a tip 104 of a needle 102 through the skin and into a tissue selected from the group consisting of a lymph node and a thoracic duct, and delivering an immune modulating agent through the needle 102 and into the tissue to treat at least one immune disorder.

The present disclosure includes disclosure of a method, wherein the step of inserting further comprises confirming a location of the tip 104 of the needle 102 within the tissue.

The present disclosure includes disclosure of a method, wherein the step of inserting further comprises confirming efferent flow from the tissue.

The present disclosure includes disclosure of a method, wherein the step of inserting further comprises securing the needle 102 into the tissue.

The present disclosure includes disclosure of a method, further comprising the step of monitoring the delivery of the immune modulating agent and detecting potential leakage outside of the tissue or the venous system during the delivery.

The present disclosure includes disclosure of a method, wherein the step of inserting is performed under ultrasound guidance.

The present disclosure includes disclosure of a method, wherein the ultrasound guidance comprises using a three-dimensional ultrasonic probe.

The present disclosure includes disclosure of a method, wherein the three-dimensional ultrasonic probe comprises a portion of a needle 102 guide system comprising the needle 102, and wherein the three-dimensional ultrasonic probe is operable while the tip 104 of the needle 102 is positioned within the tissue.

The present disclosure includes disclosure of a method, wherein the step of inserting is performed to position the tip 104 of the needle 102 at a center of the lymph node.

The present disclosure includes disclosure of a method, wherein the step of inserting is performed to position the tip 104 of the needle 102 near a hilum of the lymph node.

The present disclosure includes disclosure of a method, wherein the step of inserting is performed using photoacoustic imaging.

The present disclosure includes disclosure of a method, wherein the photoacoustic imaging comprises the step of injecting a photoacoustic contrast agent with affinity to the lymphatic system proximal to the tissue.

The present disclosure includes disclosure of a method, further comprising the use of image processing software to calculate an ideal position for the needle 102 tip 104 within the tissue after the photoacoustic contrast agent has migrated into the tissue so that the photoacoustic imaging can identify the tissue having the photoacoustic contrast agent.

The present disclosure includes disclosure of a method, performed so that efferent lymphatic vessels receive the photoacoustic contrast agent and become opaque under photoacoustic imaging.

The present disclosure includes disclosure of a method, performed so that lymph nodes having lympho-venous communications do not receive the photoacoustic contrast agent and therefore do not become opaque under photoacoustic imaging.

The present disclosure includes disclosure of a method, wherein the step of inserting is performed using impedance based upon bioimpedance differences of the skin and the tissue.

The present disclosure includes disclosure of a method, wherein the bioimpedance differences are determined using an impedance device with a first electrode and a second electrode, whereby the first electrode is located at the tip 104 of the needle 102 and whereby the second electrode is located at a proximal portion of the needle 102 or on a surface of the skin.

The present disclosure includes disclosure of a method, wherein the bioimpedance differences can detect leakage of the immune modulating agent during or after delivery into the tissue.

The present disclosure includes disclosure of a method, wherein the step of delivering is performed using impedance based upon bioimpedance differences of the skin, the tissue, and a vein.

The present disclosure includes disclosure of a method, wherein the bioimpedance differences are determined using the needle 102 as one electrode, a second electrode positioned on the skin, and a third electrode positioned within a vein.

The present disclosure includes disclosure of a method, wherein the bioimpedance differences are identified if there is leakage of the immune modulating agent into the vein.

The present disclosure includes disclosure of a method, wherein the step of inserting is performed using a motorized needle 102 device.

The present disclosure includes disclosure of a method, wherein the step of inserting comprises inserting the needle 102 that is coated with an echogenic material configured to be visualized using an external visualization mechanism.

The present disclosure includes disclosure of a method, wherein the step of delivering is performed using hydrostatic pressure.

The present disclosure includes disclosure of a method, wherein the step of delivering is performed using pressure-regulated injection.

The present disclosure includes disclosure of a method, wherein the step of delivering is performed using flow-regulated injection.

The present disclosure includes disclosure of a method, wherein the step of delivering is performed using an immune modulating agent marked with an indicator configured to be visualized under ultrasound so that potential leakage of the immune modulating agent outside of the tissue can be visualized.

The present disclosure includes disclosure of a method, wherein the step of delivering is performed using an immune modulating agent marked with an indicator configured to be visualized under photoacoustic imaging so that potential leakage of the immune modulating agent outside of the tissue can be visualized.

The present disclosure includes disclosure of a method, wherein the step of delivering is performed while a Doppler probe is positioned adjacent an iliac vein.

The present disclosure includes disclosure of a method, wherein the immune modulating agent is marked with an indicator, and wherein the Doppler probe is configured to detect a signal from the immune modulating agent within the iliac vein should the immune modulating agent leak into the iliac vein.

The present disclosure includes disclosure of a method, wherein the step of inserting is further performed to secure the tip 104 of the needle 102 within the tissue using a needle 102 securing device.

The present disclosure includes disclosure of a method, further comprising the step of identifying the tissue among a collection of tissues, the step of identifying performed before the step of inserting.

The present disclosure includes disclosure of a method, wherein the identifying step is performed by injecting a photoacoustic contrast agent with affinity to the lymphatic system proximal to the collection of tissues, and monitoring the photoacoustic contrast agent as it is received by efferent lymphatic vessels within the collection of tissues.

The present disclosure includes disclosure of a method, wherein the identifying step further comprises the step of selecting the tissue from the efferent lymphatic vessels that received the photoacoustic contrast agent.

The present disclosure includes disclosure of a method, wherein the step of delivering is performed while monitoring efferent flow of the immune modulating agent into and through the tissue using a monitoring mechanism selected from the group consisting of bioimpedance, Doppler, photoacoustic, and ultrasound.

The present disclosure includes disclosure of a method, wherein the step of delivering is performed while monitoring efferent flow of the immune modulating agent into and through the tissue.

The present disclosure includes disclosure of a method, further comprising the step of securing the needle within the tissue prior to the step of delivering the immune modulating agent.

While various embodiments of devices, systems, and methods have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method, comprising inserting a tip of a needle through the skin and into a tissue selected from the group consisting of a lymph node and a thoracic duct;

delivering an immune modulating agent through the needle and into the tissue to treat at least one immune disorder;

wherein the step of delivering is performed using impedance based upon bioimpedance differences of the skin, the tissue, and a vein; and wherein the bioimpedance differences are determined using the needle as one electrode, a second electrode positioned on the skin, and a third electrode positioned within the vein.

2. The method of claim 1, wherein the step of inserting further comprises confirming a location of the tip of the needle within the tissue.

3. The method of claim 1, wherein the step of inserting further comprises confirming efferent flow from the tissue.

4. The method of claim 1, wherein the step of inserting further comprises securing the needle into the tissue.

5. The method of claim 1, further comprising the step of:

monitoring the delivery of the immune modulating agent and detecting potential leakage outside of the tissue or the venous system during the delivery.

6. The method of claim 1, wherein the step of inserting is performed under ultrasound guidance using a three-dimensional ultrasonic probe.

7. The method of claim 1, wherein the step of inserting is performed to position the tip of the needle at a center of the lymph node.

8. The method of claim 1, wherein the step of inserting is performed to position the tip of the needle near a hilum of the lymph node.

9. The method of claim 1, wherein the step of inserting is further comprises injecting a photoacoustic contrast agent with affinity to a lymphatic system proximal to the tissue so that efferent lymphatic vessels receive the photoacoustic contrast agent and become opaque under photoacoustic imaging.

10. The method of claim 9, further comprising the use of image processing software to calculate an ideal position for the needle tip within the tissue after the photoacoustic contrast agent has migrated into the tissue so that the photoacoustic imaging can identify the tissue having the photoacoustic contrast agent.

11. The method of claim 1, wherein the step of inserting is performed using impedance based upon bioimpedance differences of the skin and the tissue.

12. The method of claim 11, wherein the bioimpedance differences are determined using an impedance device with a first electrode and a second electrode, whereby the first electrode is located at the tip of the needle and whereby the second electrode is located at a proximal portion of the needle or on a surface of the skin.

13. The method of claim 11, wherein the bioimpedance differences can detect leakage of the immune modulating agent during or after delivery into the tissue.

14. The method of claim 1, wherein the step of inserting comprises inserting the needle that is coated with an echogenic material configured to be visualized using an external visualization mechanism.

15. The method of claim 1, wherein the step of delivering is performed using an immune modulating agent marked with an indicator configured to be visualized under ultrasound so that potential leakage of the immune modulating agent outside of the tissue can be visualized.

16. The method of claim 1, wherein the step of delivering is performed using an immune modulating agent marked with an indicator configured to be visualized under photoacoustic imaging so that potential leakage of the immune modulating agent outside of the tissue can be visualized.

17. The method of claim 1, further comprising the step of:

securing the needle within the tissue prior to the step of delivering the immune modulating agent.

* * * * *